United States Patent [19]

Günther et al.

[11] Patent Number: 5,248,798

[45] Date of Patent: Sep. 28, 1993

[54] METHOD OF PREPARATION OF 8-HYDROXYOCTANOIC ACID

[75] Inventors: Bernd R. Günther, Bergheim; Rainer Losch, Bonn; Hans Lautenschläger; Klaus Steiner, both of Pulheim, all of Fed. Rep. of Germany

[73] Assignee: Natterman, A. & Cie. GmbH, Cologne, Fed. Rep. of Germany

[21] Appl. No.: 730,854

[22] PCT Filed: Jan. 19, 1990

[86] PCT No.: PCT/EP90/00105

§ 371 Date: Jul. 22, 1991

§ 102(e) Date: Jul. 22, 1991

[87] PCT Pub. No.: WO90/08125

PCT Pub. Date: Jul. 26, 1990

[30] Foreign Application Priority Data

Jan. 21, 1989 [DE] Fed. Rep. of Germany ....... 3901801

[51] Int. Cl.$^5$ ............................................. C07C 57/00
[52] U.S. Cl. .................................................... 554/150
[58] Field of Search ................. 260/408, 413; 554/150

[56] References Cited

U.S. PATENT DOCUMENTS 3,404,166 10/1968 Achard et al. ...................... 260/413
3,708,534 1/1973 Ishimoto et al. .................... 260/535

FOREIGN PATENT DOCUMENTS 1355775 2/1964 France .

OTHER PUBLICATIONS

Chemical Abstracts, vol. 104, #11, p. 620, 1986.

*Primary Examiner*—José G. Dees
*Assistant Examiner*—D. D. Carr
*Attorney, Agent, or Firm*—Burns, Doane, Swecker & Mathis

[57] ABSTRACT

The invention refers to a novel method for the preparation of 8-hydroxyoctanoic acid by reaction of 6-chlorohexanol with a dialkyl malonate ester, thermal decarboxylation of the malonic acid derivative and isolation of the 8-hydroxyoctanoic acid as the free acid or as an alkali metal salt.

16 Claims, No Drawings

METHOD OF PREPARATION OF 8-HYDROXYOCTANOIC ACID

DESCRIPTION

The present invention refers to a novel and advantageous method of preparation of 8-hydroxyoctanoic acid with formula I and its salts $$HO-(CH_2)_7-COOR \qquad (I)$$

where R represents hydrogen or an alkali metal atom.

DESCRIPTION OF THE PRESENT STATE OF THE ART

ω-Hydroxycarboxylic acids with 2–6 carbon atoms together with their salts, esters and lactones are established technical products; ω-hydroxycarboxylic acids with 9–11 carbon atoms are obtained, in part, semisynthetically from natural products (oleic acid, castor oil etc.), higher members are prepared, for example, by the reaction of cyclic enamines with ω-acyloxycarboxylic acid chlorides (cf. G. Schill, Chem. Ber. 99, 2689 (1966).

Some methods are also known for the preparation of 7-hydroxyheptanoic acid and 8-hydroxyoctanoic acid. Thus, 7-hydroxyheptanoic acid is accessible from 7-chloroheptanoic acid (A. N. Nesmeyanov, L. I. Zakharkin, Izvest. Akad. Nauk. U.S.S.R., Otdel. Khim. Nauk. 1955, 224-32; Bull. Acad. Sci. U.S.S.R., Div. Chem. Sci. 1955, 199-205 (C.A. 1956, 4849)), furanacrylic acid (E. V. Hort, U.S. Pat. No. 2,955,133 (1960)), alkoxytetrahydropyranes (A. E. Montagna, D. G. Kubler, J. J. Brezinski, U.S. Pat. No. 2,998,466 (1961)) or from cycloheptanone by Baeyer-Villiger oxidation (Neth. Appl. 6511967 (1966), C.A. 65, 3995h (1966); R. Robinson, L. H. Smith, J. Chem. Soc. 1937, 371–4).

8-Hydroxyoctanoic acid which is a component of gelée royale (cf. N. Weaver, N. S. Johnston, R. Benjamin, J. H. Law, Lipids 3, 535–8 (1968), C.A. 70, 55231b (1969)) and its esters can, apart from some low-yield routes (from octanoic acid, cf. M. Kusunose, E. Kusunose, H. J. Coon, J. Biol. Chem. 239, 1374–80 (1964); from the nitrile of oleic acid, cf. J. Pasero, L. Comeau, M. Naudet, Bull. Soc. Chim. France 1963, 1794–8; from octandioic acid by reduction with hydrogen, cf. A. N. Bashkirov, L. A. Morozov, A. I. Prudnikov, Neftekhimiya 16, 230–4 (1976), C.A. 85, 77548x (1976); via the methyl ester of 8-acetoxy-6-oxooctanoic acid or its ethylenethioketal, cf. S. Yurugi et al., Ann. Rep. Takeda Res. Lab. 27, 34–42, (1968), C.A. 70, 77899c (1969), H. Hagiwara et al., Japan Patent 19323 (65), C.A. 1965, 16218c; from the lactam of N-nitroso-8-aminooctanoic acid, cf. R. Huisgen, J. Reinertshofer, Justus Liebigs Ann. Chem. 575, 174-97 (1952), C.A. 47, 3812h; via β-2-thenoylpropionic acid, cf. E. Schwenk et al., Org. Syntheses 27, 68–71, (1947)), be prepared by the reduction of octandioic monoester acid chloride with sodium borohydride (H. J. Bestmann, R. Kunstmann, H. Schulz, Justus Liebigs Ann. Chem. 699, 33–9 (1966), C.A. 66, 54981b (1967)), by the reduction of the potassium salt of octandioic acid monomethyl ester with sodium in ethanol (P. Chuit and J. Hausser, Helv. Chim. Acta 12, 463–92, (1929), C.A. 23, 3663 (1929)), via the oxidation of 6-chlorohexanol to 6-chlorohexanal, condensation of the aldehyde with malonic acid, decarboxylation to 8-chloro-2-octenoic acid, conversion to 8-hydroxy-2-octenoic acid and hydrogenation of the double bond (R. Achard and J. Morel, Fr. 1355775, C.A. 61, 4222h (1964)) or by Baeyer-Villiger oxidation of cyclooctanone (Neth. Appl. 6511967, C.A. 65, 3995h (1966); E. E. Smissman, J. F. Muren, N. A. Dahle, J. Org. Chem. 29, 3517-20 (1964), C.A. 62, 2703a (1965); S. L. Friess and P. E. Frankenburg, J. Am. Chem. Soc. 74, 2679 (1952)).

A further synthetic route to 8-hydroxyoctanoic acid and its salts starting from 1,6-dichlorohexane and dialkyl malonates has been described by H. Lautenschläger et al. (DE-OS 34 01 913).

The 8-hydroxyoctanoic acids and their salts are valuable intermediates for the synthesis of pharmacologically active 2-imidazolyloxyalkane carboxylic acids and in particular octimibate (H. Lautenschläger et al., DE-OS 32 28 271).

The purpose of this invention is to provide a preparation method for 8-hydroxyoctanoic acid and/or its salts that requires less expense than present methods and which is characterized by a better overall yield.

This purpose is achieved by:

Method for the preparation of 8-hydroxyoctanoic acid and its salts according to formula I $$HO-(CH_2)_7-COOR \qquad (I)$$

Where R represents hydrogen or an alkali metal atom, characterized by reacting (i) 6-chlorohexan-1-ol of formula II $$Cl-(CH_2)_6OH \qquad (II)$$

with dialkyl malonate ester in stoichiometric ratio in potassium or sodium alcoholate solution of a lower alcohol at the reflux temperature of the reaction mixture, (ii) followed by distilling off the alcohol, taking up the residue remaining in water and neutralizing with acid, (iii) extracting with a water-immiscible organic solvent and then removing the solvent after separating off the aqueous phase, (iv) deesterifying the residue from step (iii) with formic acid in the presence of an acidic catalyst, (v) decarboxylating the malonic acid derivative so formed by heating to 120° to 150° C., (vi) heating the product so formed under reflux with aqueous alkali metal hydroxide solution, (vii) then extracting with a water-immiscible solvent, (viii) adjusting the aqueous phase to pH 2-3 with a mineral acid and extracting the 8-hydroxyoctanoic acid so liberated with ethyl acetate and isolating it or converting it to the alkali metal salt of formula I by treatment with alcoholic alkali metal hydroxide solution.

The reactions involved in the preparation take place according to scheme 1:

Scheme 1

$$\begin{array}{c} R^1OOC \\ \phantom{R^1OOC}\diagdown \\ \phantom{R^1OOC}\phantom{xx}CH_2 + Cl-(CH_2)_6-OH \xrightarrow{R^2ONa/EtOH} \\ \phantom{R^1OOC}\diagup \\ R^1OOC \end{array}$$

$$HO-(CH_2)_7-COOH \xrightarrow{ROH} HO-(CH_2)_7-COOR$$

$R^1$ = straight chain or branched chain $C_1$-$C_4$-alkyl
$R^2$ = $CH_3$— or $C_2H_5$—

Surprisingly it was found that the easily accessible and industrially available 6-chlorohexan-1-ol of formula II

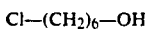

can react in a dropwise addition reaction with dialkyl malonate esters in good yield and without isolation of the intermediate products to yield 8-hydroxyoctanoic acid.

In this new preparation method a dialkyl malonate ester, such as for example dimethyl malonate, dipropyl malonate, diisopropyl malonate, dibutyl malonate, diisobutyl malonate and especially diethyl malonate is reacted with 6-chlorohexan-1-ol in a methanolic or ethanolic solution of alkali metal alcoholate, especially sodium alcoholate solution or potassium alcoholate solution to yield the dialkyl 6-hydroxyhexylmalonate. The concentration of the 6-chlorohexanol can be 15 to 30% by weight, preferably 20% by weight, of the solution. The crude dialkyl ester of 6-hydroxyhexylmalonic acid extracted from the residue of the reaction mixture is deesterified with formic acid in the presence of an acidic catalyst, preferably p-toluenesulfonic acid. The malonic acid derivative produced is then decarboxylated without further purification in the absence of solvent in an inert gas atmosphere, if desired under gentle vacuum of 0.1 to 1.0 bar, treated with aqueous sodium hydroxide solution or potassium hydroxide solution and then extracted under alkaline conditions with an organic solvent preferably an aromatic solvent such as benzene, toluene or xylene. After alkaline extraction the 8-hydroxyoctanoic acid is liberated from the aqueous phase in the usual manner with the aid of mineral acids, preferably dilute hydrochloric acid, extracted with an organic solvent and isolated. The free acid has only limited stability on account of its tendency to form oligomers in the presence of traces of mineral acids. It is, therefore, preferable to react this with an alcoholic alkali metal hydroxide solution in order to form the alkali metal salt of 8-hydroxyoctanoic acid and then precipitate out this alkali metal salt. For this purpose it is preferable to use potassium hydroxide or sodium hydroxide in 2-propanol. The product so obtained is of sufficient purity and is stable.

It is of importance for this new process that 6-chlorohexan-1-ol is reacted at reflux temperature with a dialkyl malonate ester in stoichiometric ratio in the presence of an alkali metal alcoholate solution of a lower alcohol, preferably sodium ethylate or sodium methylate, that after the alcohol is distilled off the residue that remains is neutralized with acid after being taken up in water, whereby HCl, $H_2SO_4$, $H_3PO_4$ and $HNO_3$ are suitable acids, where the organic solvent used for extraction is preferably ethyl acetate, that after removal of solvent the residue is deesterified by formic acid in the presence of an acidic catalyst, preferably p-toluenesulfonic acid, that the malonic acid derivative so produced is preferably decarboxylated at 135°–145° C., if desired under a slight vacuum, that the crude product obtained after decarboxylation is treated by boiling under reflux with an aqueous alkali metal hydroxide solution, preferably dilute sodium hydroxide solution, that after alkaline treatment the alkaline solution is extracted with an aromatic solvent, preferably toluene, that after extraction the solution is adjusted to pH 2–3 with a mineral acid, preferably dilute hydrochloric acid and then extracted with ethyl acetate, that after dissolution in alcohol, preferably 2-propanol, the 8-hydroxyoctanoic acid is transformed into the corresponding alkali metal salt by treatment with an alcoholic solution of an alkali metal salt, preferably potassium hydroxide in 2-propanol.

Aromatic sulfonic acids, such as p-phenolsulfonic acid and p-toluenesulfonic acid, are especially suitable as acid catalysts for the cleavage of the ester. Catalytic quantities are 2–20% by weight with respect to the amount of 6-chlorohexan-1-ol employed. In order to remove by-products the residue remaining after decarboxylation is taken up in aqueous alkali metal hydroxide solution with heating and the by-products are removed by extraction with an organic solvent.

Dilute aqueous mineral acids, such as HCl, $H_2SO_4$, $HNO_3$ and $H_3PO_4$, are suitable for liberation of the 8-hydroxyoctanoic acid. The stable alkali metal salt can be formed from the free 8-hydroxyoctanoic acid by reacting the acid with alkali metal hydroxides such as sodium hydroxide or potassium hydroxide. A reaction in solution is preferred whereby the acid is dissolved in a lower, water-miscible alcohol and precipitated as the salt by the addition of alcoholic alkali metal hydroxide solutions and isolated.

The process to which the invention relates exhibits many advantages over known processes.

These include:
a) better total yield
b) less complex apparatus
c) lower costs
d) the absence of expensive high-vacuum distillation
e) the absence of expensive catalysts
f) lower technical safety requirements
g) easily disposable waste products The process to which the invention relates will be further described by means of the following example.

EXAMPLE

In a 4 l four-neck round-bottomed flask fitted with thermometer, vacuum-sealed stirrer, addition vessel and reflux condenser are placed 1830 g sodium ethylate solution (21%) and heated to 70° C. Then 824 g (5.14 mol) diethyl malonate is added with stirring. This is followed by 704 g (5.14 mol) 6-chlorohexan-1-ol and the mixture is heated under reflux with stirring for ca. 8 hours. After distilling off the ethanol the residue is taken up in ca. 1700 ml water and neutralized with dilute hydrochloric acid. The neutral aqueous phase is extracted with a total of ca. 3 l ethyl acetate. After distilling off the ethyl acetate the residue is treated with ca. 3240 g formic acid and ca. 98.5 g p-toluenesulfonic acid monohydrate in the reactor described above that has been modified by replacing the reflux condenser with a distillation head. The solution is heated to ca. 100°–105° C. with stirring. The ethyl formate produced during the reaction is distilled off azeotropically with formic acid over a period of ca. 9 hours. After removal of the excess formic acid by distillation the residue that remains is decarboxylated for ca. 10 h at ca. 140° C. under nitrogen in a gentle vacuum. After cooling the residue is taken up into a solution of ca. 300 g sodium hydroxide in ca. 3 l water and boiled under reflux for ca. 3 hours. After allowing to cool to room temperature the alkaline phase is extracted 3 times with ca. 1 l portions of toluene. The aqueous phase is then adjusted to ca. pH 2 by the addition of dilute hydrochloric acid. The oily precipitate of 8-hydroxyoctanoic acid is extracted 3 times with ca. 1 l portions of ethyl acetate. The combined ethyl acetate phases are treated with ca. 30 g active charcoal, clarified by filtration and the ethyl acetate removed by distillation.

(Residue ca. 585 g = 71% of th.)

The residue obtained as above is dissolved in ca. 1.5 l 2-propanol. To this is added a solution of ca. 205 g potassium hydroxide in ca. 1 l 2-propanol. The temperature of the reaction mixture rises thereby to ca. 50° C. and is allowed to cool to room temperature during stirring. The product that precipitates out is filtered off by suction and then washed with a total of ca. 0.3 l 2-propanol and ca. 0.4 l petroleum ether (40–60). The filter cake is dried in the vacuum drying cupboard at 50°–70° C. and ca. 0.1 bar until its weight is constant.

Yield 460 g = 45.1% with respect to 6-chlorohexan-1-ol

We claim:

1. Method for the preparation of 8-hydroxyoctanoic acid and its salts according to formula I

$$HO-(CH_2)_7-COOR \qquad (I)$$

where R represents hydrogen or an alkali metal atom, characterized by (i) reacting 6-chlorohexan-1-ol of formula II

$$Cl-(CH_2)_6OH \qquad (II)$$

with dialkyl malonate esters in stoichiometric ratio in potassium or sodium alcoholate solution of a lower alcohol at the reflux temperature of the reaction mixture, (ii) followed by distilling off the alcohol, taking up the residue remaining in water and neutralizing with acid, (iii) extracting with a water-immiscible organic solvent and then removing the solvent after separating off the aqueous phase, (iv) deesterifying the residue from step (iii) with formic acid in the presence of an acidic catalyst, (v) decarboxylating the malonic acid derivative so formed by heating to 120° to 150° C., (vi) heating the product so formed under reflux with aqueous alkali metal hydroxide solution, (vii) then extracting with a water-immiscible solvent, (viii) adjusting the aqueous phase to pH 2–3 with a mineral acid and extracting the 8-hydroxyoctanoic acid so liberated with ethyl acetate and isolating it or converting it to the alkali metal salt of formula I by treatment with alcoholic alkali metal hydroxide solution.

2. Methods according to claim 1, wherein an ethanolic or methanolic alkali metal alcoholate solution containing 15% to 30% by weight 6-chlorohexan-1-ol as a proportion of the total solution is employed.

3. Methods according to claim 1, wherein p-toluenesulfonic acid is used as acidic catalyst to cleave the ester.

4. Methods according to each of the previous claims, wherein the decarboxylation is carried out in an atmosphere of inert gas at a pressure of 0.1 to 1.0 bar.

5. Methods according to claim 1, wherein an aromatic solvent is used as the extraction agent in step (vii).

6. The method according to claim 5, wherein said aromatic solvent is selected from the group consisting of benzene, toluene and xylene, mixtures thereof.

7. The method according to claim 1, wherein said mineral acid comprises hydrochloric acid.

8. The method according to claim 1, wherein said alcoholic alkali metal hydroxide solution comprises potassium hydroxide or sodium hydroxide in 2-propanol.

9. The method according to claim 1, wherein said potassium or sodium alcoholate solution is comprised of sodium ethylate or sodium methylate.

10. The method according to claim 1, wherein said residue remaining in water is neutralized with HCl, $H_2SO_4$, $H_3PO_4$ or $HNO_3$.

11. The method according to claim 1, wherein said water-immiscible organic solvent used for extraction is ethyl acetate.

12. The method according to claim 1, wherein said residue from step (iii) is deesterified with formic acid in the presence of an aromatic sulfonic acid.

13. The method according to claim 12, wherein said aromatic sulfonic acid is selected from the group consisting of p-phenolsulfonic acid or p-toluenesulfonic acid, or mixtures thereof.

14. The method according to claim 1, wherein said malonic acid derivative is decarboxylated by heating to a temperature of 135° to 145° C. under a slight vacuum.

15. The method according to claim 1, wherein said aqueous alkali metal hydroxide solution is comprised of sodium hydroxide.

16. The method according to claim 1, wherein the 8-hydroxyoctanoic acid is prepared without isolation of the intermediate products by reacting the compound of formula II in a dropwise addition reaction with said dialkyl malonate esters.

* * * * *